United States Patent
Armstrong et al.

(10) Patent No.: US 8,784,708 B2
(45) Date of Patent: Jul. 22, 2014

(54) CUSTOM-FITTED PROSTHETIC SOCKET DEVICES AND METHODS FOR PRODUCING SAME

(76) Inventors: Peter Armstrong, Portland, OR (US); Wayne Armstrong, Portland, OR (US)

( * ) Notice: Subject to any disclaimer, the term of this patent is extended or adjusted under 35 U.S.C. 154(b) by 0 days.

(21) Appl. No.: 13/352,208

(22) Filed: Jan. 17, 2012

(65) Prior Publication Data

US 2012/0116539 A1    May 10, 2012

Related U.S. Application Data

(60) Provisional application No. 61/461,213, filed on Jan. 17, 2011.

(51) Int. Cl.
  *A61F 2/80* (2006.01)
  *A61F 2/50* (2006.01)
  *B29C 44/12* (2006.01)

(52) U.S. Cl.
  CPC ........... *B29C 44/1204* (2013.01); *A61F 2/5046* (2013.01); *A61F 2/80* (2013.01)
  USPC .............. 264/46.5; 264/261; 623/27; 623/36; 623/33

(58) Field of Classification Search
  USPC .......................... 264/261, 46.5; 623/27, 36, 33
  See application file for complete search history.

(56) References Cited

U.S. PATENT DOCUMENTS

| | | | | |
|---|---|---|---|---|
| 4,817,590 A | * | 4/1989 | Stancik, Jr. ....................... | 602/8 |
| 5,503,543 A | * | 4/1996 | Laghi ................................ | 425/2 |
| 2008/0004715 A1 | * | 1/2008 | Asgeirsson ..................... | 623/33 |

* cited by examiner

*Primary Examiner* — Galen Hauth
(74) *Attorney, Agent, or Firm* — Mohr Intellectual Property Law Solutions, PC

(57) ABSTRACT

Methods of producing a custom-fitted prosthetic socket device for a residual limb include covering the distal end thereof with a liner, positioning the covered end within a socket cup to maintain a spaced relationship between the exterior of the liner and the interior of the socket cup, introducing an expandable, hardenable filler material into the socket cup, expanding the material to fill the volume between the liner and the socket cup, hardening the material, and removing the socket cup, hardened filler material, and liner, from the residual limb. Some methods include a filler material that hardens into a flexible solid foam cushioning layer which may optionally form a bond between the socket cup and the liner, embedding the liner in the cushioning layer. Some methods include selecting a socket cup from a plurality of sized socket cups, and/or providing the plurality of sized socket cups.

20 Claims, 1 Drawing Sheet

CUSTOM-FITTED PROSTHETIC SOCKET DEVICES AND METHODS FOR PRODUCING SAME

RELATED APPLICATION

This application claims the benefit of U.S. Provisional Application No. 61/461,213, filed on Jan. 17, 2011, the entire disclosure of which is incorporated herein by reference for all purposes.

TECHNICAL FIELD

This disclosure relates to prosthetics, and in particular to prosthetic socket devices that are custom-fitted to a user's residual limb, for use with a prosthetic device.

BACKGROUND

Prosthetic socket devices for fitting prostheses to residual limbs of amputees are traditionally by creating a male or positive mold of the residual limb area made from a female or negative casting sleeve formed by molding the sleeve directly against the residual limb, usually with the aid of a pressure casting system. The positive mold is then adjusted or "rectified," such as to provide relief for sensitive areas of the residual limb, to obtain a correctly-sized socket that will fit the residual limb, and so forth. Finally, a socket is constructed based on the adjusted positive mold.

The traditional multiple-step molding and rectification process summarized above is extremely simplified; however, in practice the procedure is time-consuming and expensive, and heavily dependent on the individual skills of the prosthetist. Moreover, it is standard that different individuals handle different parts of the production process. For example, socket construction is typically performed by personnel working at a specialized lab, once the positive mold is complete. The additional personnel and transportation involved in the standard process contribute to the overall time and expense, even more so in small, remote, and/or socioeconomically disadvantaged rural locations.

SUMMARY

The methods disclosed herein describe a process for making a custom-fitted prosthetic socket that avoids much of the complication and expense of standard procedures, and which may be performed on-site by a practitioner using readily-available materials. Further, in many embodiments, custom-fitted prosthetic socket may be created in a matter of hours (or in even less time), rather than days or weeks.

Briefly, an illustrative example of a custom-fitted prosthetic socket produced according to the present disclosure may include a socket cup having an open end and a closed end, a foam cushioning layer bonded to the interior surface of the socket cup, and a residual limb liner having a closed, distal end embedded into the foam cushioning layer and spaced from the interior surface of the socket cup thereby, with the open, proximal end protruding from the open end of the socket cup. The interior surface of the residual limb liner defines a volume adapted to receive and securely fit a distal end region of a user's residual limb. At least a portion of the exterior surface of the socket cup, typically the closed, distal end, is adapted to couple with a prosthetic device (e.g. either by directly coupling to a prosthesis, or indirectly by means of intervening coupling structure).

The example socket device summarized above, and others constructed according to the present disclosure, may be produced by means of illustrative methods disclosed herein, which may include selecting a socket cup (e.g. from a plurality or series of socket cups of different sizes and/or shapes) appropriate to the physical configuration of the distal end region of a user's residual limb, covering the distal end region of the residual limb with a limb liner having a porous exterior surface, and positioning the covered distal end region within the socket cup. Once positioned, methods may proceed by introducing an expandable, hardenable filler material, such as a polyurethane foam, into the socket cup, and maintaining a spaced relationship between the exterior surface of the limb liner and the interior surface of the socket cup while allowing the filler material to expand to fill the volume therebetween. The material may at least partially permeate the porous exterior surface of the limb liner, such that when the filler material hardens, it forms a bond between the interior surface of the socket cup and the limb liner, and also provides a flexible, yet supportive cushioning layer. The socket cup, cushioning layer, and embedded limb liner may then be removed from the residual limb as a unitary prosthetic socket device, and coupled to (and used with) a prosthetic device.

Several variations to the example illustrative method summarized above are possible and are considered to be within the scope of this disclosure. For example, some methods may further include providing (e.g. producing) the plurality or series of socket cups. Further, a filler material that hardens into a flexible solid foam to form the foam cushioning layer, for example an integral skinning polyurethane foam, is generally formed by mixing two or more reactive components in a certain ratio to produce a solid foam of a predetermined density, which relates to the flexibility or resilience of the hardened solid foam. In methods using such a filler material, the material may consist of two or more mixtures of the reactive compounds in different ratios, such as to produce areas (or volumes) of different densities in the flexible solid foam cushioning layer formed thereby.

The concepts, features, methods, and component configurations briefly described above are clarified with reference to the accompanying drawings and detailed description below.

DETAILED DESCRIPTION

Figures 1, 2:
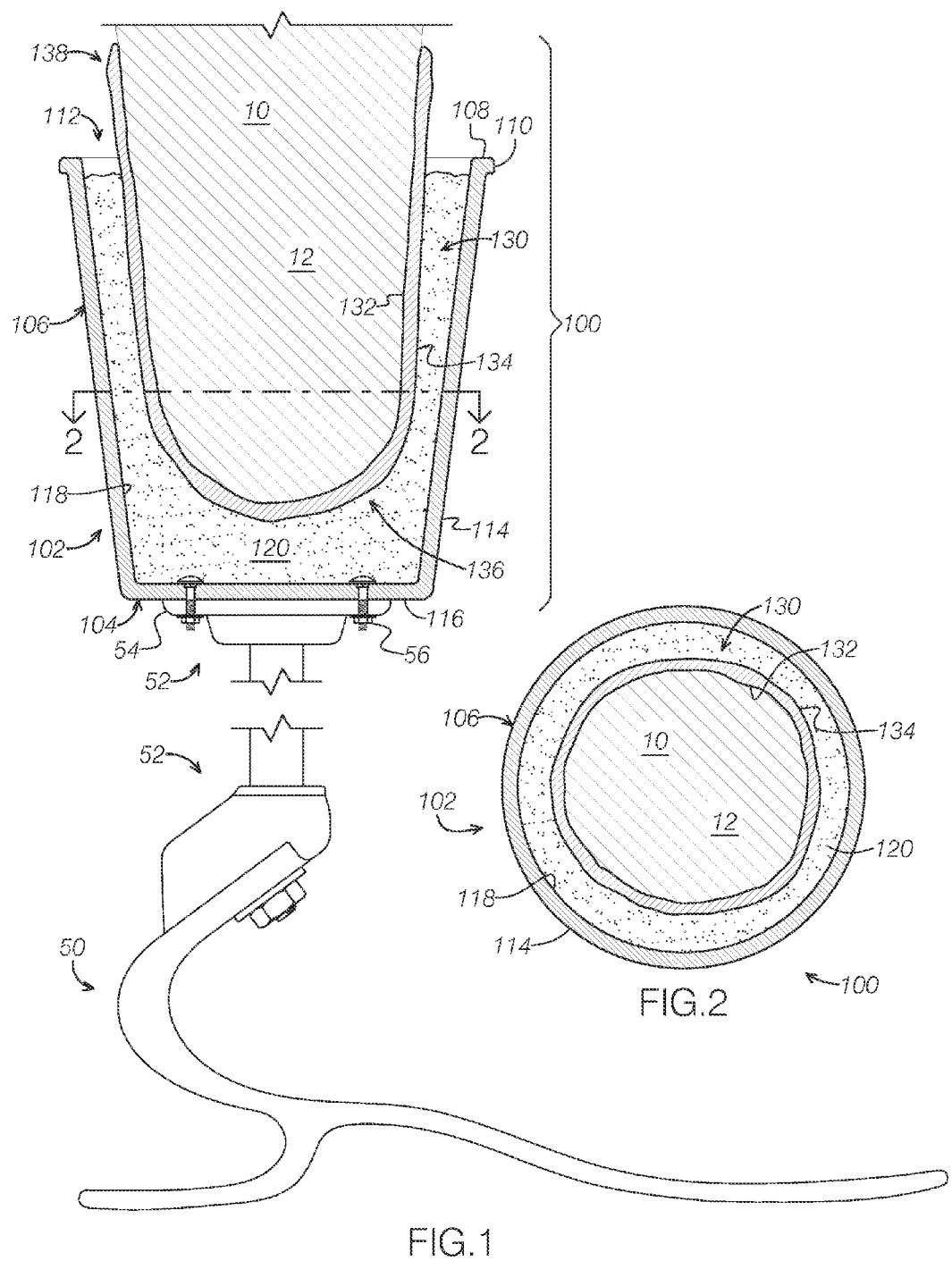
FIG. 1 shows a side elevation view, in cutaway, of an illustrative example of a custom-fitted prosthetic socket device constructed in accordance with aspects of the present disclosure, joining a residual limb to a prosthetic foot device.
FIG. 2 shows a cross-sectional view of the example prosthetic socket device of FIG. 1, taken along the line 2-2 of FIG. 1.

In this description, orientational and directional terms such as "left," "right," "top," "bottom," and so forth, are used for clarity of illustration and generally refer to the relative positions of components and other objects illustrated in the drawings, but are not intended to be limiting, as the prosthetic socket devices disclosed herein (and components thereof) are not restricted to the orientations and positions shown in the drawings. Moreover, for ease of explanation, the example prosthetic socket devices disclosed herein are described and illustrated for use with a residual leg limb, such as may result from a transtibial or below-the-knee, amputation, a congenital anomaly, or otherwise, and for supporting a prosthetic foot device. However, the concepts and methods disclosed herein are applicable for production of prosthetic socket devices appropriate for use with residual limbs (and prostheses) of various types.

FIG. 1 illustrates an example of a custom-fitted prosthetic socket device, designated generally at 100, adapted to fit a residual limb 10, or more specifically a distal end region 12 thereof, and support a prosthetic device 50 thereon. Socket device is shown to include an open-ended socket cup 102 defined by a floor 104 and a wall 106, with the top edge 108 of the wall defining a slight annular lip 110 and forming an opening 112 in the top end of the cup 102. As described in greater detail below, cup 102 may be fabricated from a lightweight, mechanically durable, and substantially rigid material such as any of several suitable plastics, a metal such as aluminum, and so forth.

A portion of the exterior surface 114 of cup 102, specifically the exterior face 116 of the floor 104, is shown to couple the socket device 100 to prosthetic device 50 via coupling structure (generally indicated at 52) in a conventional manner, such as via a support plate 54 fastened to floor 104 via fastening components 56 shown as standard bolt and nut fittings. Support plate 54 is, in turn, secured either directly or via further coupling components, to prosthetic device 50.

To the interior surface 118 of cup 102 is bonded a foam cushioning layer 120. As described in greater detail below, foam cushioning layer 120 is generally a flexible solid material such as a polyurethane foam having a predetermined density. The flexibility, or resilience, of the foam cushioning layer is to some extent a function of its density; in turn, the density is to some extent a function of the filler material used to form the cushioning layer. As described in greater detail below, an example filler material suitable for use in the example methods and socket devices disclosed herein is an expandable, hardenable material such as a polyurethane foam that is created by mixing two reactive components in a ratio that may determine the density of the expanded hardened product.

As such, the density of the cushioning layer may be uniform throughout the entirety of the layer; optionally, the layer may include regions of different densities (resulting in regions having different degrees of resilience). For example, pressure relief regions in the cushioning layer, such as to accommodate sensitive areas of residual limb 10, may be formed by using a comparatively lower-density mixture of filler material, whereas other regions, such as might benefit from a less-flexible material, may be formed by using a comparatively higher-density mixture of the filler material, and so forth.

The distal end region 12 of residual limb 10 is shown to be covered with a residual limb liner 130, such as is known in the art. Limb liners such as limb liner 130 are generally thought to improve patient safety, comfort, and hygiene by adding a supportive, resilient layer between the residual limb and traditional prosthetic sockets. Many choices in liner technology are available; most are made with a synthetic, resilient material on the interior surface that interfaces with the skin (examples include silicones, urethanes or other thermoplastic elastomers, mineral oil derivatives and/or gels, and so forth), and a porous material on the exterior surface (such as one or more natural or synthetic fabrics). Although many types of limb liners may be used, example limb liners suitable for use with, and incorporation into, the prosthetic socket devices of the present disclosure are those of the Alpha® Classic line of limb liners produced by The Ohio Willow Wood Company, Inc. of Mt. Sterling, Ohio. Accordingly, limb liner 130 includes a thermoplastic elastomer gel interior surface 132 and a porous exterior surface 134.

The exterior surface of the closed, distal end 136 of the liner 130 at least partially embedded in the filler material 120. As described in greater detail below, the embedding is typically accomplished by allowing the filler material to at least partially permeate the porous exterior surface 134 of a limb liner 130 while expanding and/or hardening or otherwise curing. As such, FIG. 1 is partially schematic in that the interface between the exterior surface 134 of the limb liner 130 and the cushioning layer 120 is shown as a solid line; in actuality the interface may be an overlap region having a variable thickness, given that the cushioning layer penetrates the porous exterior surface of the liner.

Although not required to all embodiments, FIG. 1 shows that the open, proximal end 138 of the limb liner 130 extends along the residual limb 10 beyond the proximal edge 108 of the socket cup. The extent to which the limb liner extends beyond the socket cup may be a function of several variables, including user comfort, user preference, the physical configuration of the distal end region of the residual limb, the size and shape of the socket cup, and so forth. For example, the prosthetic socket device 100 may be retained against the residual limb 10 mainly by the friction fit between the interior surface 132 of the limb liner 130 and the skin of the residual limb 10, but also to some extent by a compression fit of the limb liner against the residual limb, as well as suction, if the limb liner is airtight.

The relative strengths of these various retaining forces may be adjusted in several ways. For example, the variety and range of the material(s) forming the interior surface of the limb liner provide a corresponding variety of fits, by the nature of the interface of the material with skin. As such, a limb liner may be chosen to provide a desired amount of "tack." As another example, covering the distal end region of the residual limb with a fabric sock or secondary liner (not shown) before placing the residual limb into the socket device may provide a weaker friction fit than that between the user's skin and the interior surface of the limb liner embedded into the socket device. Increasing or decreasing the interface area between the limb liner and the residual limb may also affect the security of the fit. As such, constructing the socket device so that the limb liner extends further along the residual limb than the filler material and/or socket cup may provide the option for a more secure fit than a socket device without such a feature.

To remove the socket device 100 from the residual limb 10, the open end of the limb liner is typically rolled toward the distal end of the residual limb so that the friction fit is broken and the socket device 100 may be removed.

An example process of producing a custom-fitted prosthetic device for a residual limb, such as prosthetic device 100, and several variations thereof, is described in the following paragraphs.

The process may begin by selecting a socket cup such as socket cup 102. Socket cup 102 of example prosthetic socket device 100 is shown as generally frustoconical, with a tapering circular cross-section and a flat floor 104, a configuration that substantially follows the contour of most residual limbs. However, this configuration is not required to all embodiments, as a socket cup may instead be cylindrical, many-sided, rounded on the bottom, and so forth. In general, a suitable socket cup will accommodate the distal end region of the residual limb to be fitted with approximately ½" to 1½" of clearance between the residual limb, when covered with a limb liner, and the interior surface of the socket cup. However, even this range may be varied, such as if a cushioning layer of greater or lesser thickness is desired, and so forth.

The socket cup may be selected from a plurality of socket cups, such as a series of sized socket cups that may differ from each other by dimensional and/or proportional characteristics such as the diameter of the opening, the depth of the socket cup, and so forth, in a manner analogous to sizing systems used for various medical devices that are worn on the body. Socket cups may be inexpensively produced by known techniques from a variety of lightweight, mechanically durable, and substantially rigid materials such as any of several suitable plastics, a metal such as aluminum, and so forth, and, when made available to practitioners in sets of standard sizes, may allow an expedient and simple determination of a suitable size for a fitting.

Moreover, socket cups may be fabricated to couple with standard coupling structure for a prosthetic device, such as by including features such as mounting holes (as shown in example prosthetic socket device 100) or other physical characteristics suitable to mate, either directly or indirectly, with the prosthetic device for use with the residual limb. For example, mounting holes may be pre-drilled into the socket cups during fabrication. Optionally, the socket cup may be provided with suitable mounting means after the prosthetic socket device has been made, such as by the practitioner. Suitable mounting means may include any manner of fastening the socket cup to coupling structure of or for the prosthetic device, including one or more of a mechanical, magnetic, and adhesive bond, and so forth.

Once a socket cup is selected, the distal end region of the residual limb is covered with a suitable limb liner, such as limb liner 130. As indicated above, an example limb liner may be any of the Alpha® Classic line of limb liners produced by The Ohio Willow Wood Company, Inc. of Mt. Sterling, Ohio. In many cases, the limb liner 130 will have a porous exterior surface, but this is not required to all embodiments.

The process may continue by positioning the covered distal end region of the residual limb into the socket cup to maintain a spaced relationship between the exterior surface of the limb liner and the interior surface of the socket cup.

Once positioned, an expandable, hardenable filler material may be introduced into the socket cup. The filler material expands and hardens to form the cushioning layer between the socket cup and the limb liner. As noted above, example filler materials include any of several polyurethane foams, which cure to form a solid, flexible foam mass. A suitable material that has been found to provide suitable rigidity for support while offering sufficient resilience for user comfort is TC-280 A/B, available from BJB Enterprises, Inc., of Tustin, Calif. TC-280 A/B is a flexible, integral skinning polyurethane foam which, like many such materials, is created by mixing two reactive compounds (specifically, a polyurethane resin and a polyurethane curing agent).

One benefit of using a filler material such as a polyurethane foam is the rapid rise time (generally in the range of 1-10 minutes) and demold time (generally in the range of 20 minutes to 1 hour). Thus, user discomfort during the fitting process may be reduced because the residual limb generally does not need to be braced or held in place relative to the cup for long periods of time, as may be required with traditional fitting methods. Moreover, the comparatively short mold and cure time of the filler material results in a completed prosthetic limb socket in a much shorter time than according to traditional methods.

In some embodiments, the filler material not only expands to fill the space between the limb liner and the interior surface of the socket cup, but also functions to form a chemical and/or mechanical bond between the limb liner and the socket cup when the expanded material hardens. For example, a socket cup fabricated from a suitable material, such as any of several plastics, may bond with the polyurethane foam formed by the filler material. Moreover, the filler material may at least partially permeate the exterior surface of the limb liner, effectively anchoring or embedding the limb liner in the hardened product, if the exterior liner surface is porous.

Optionally, a bonding agent may be applied to one or more of the surfaces with which the filler material interfaces, prior to the introduction of the filler material into the socket cup. Of course, in some methods, bonding may not be desired until the filler material is molded to form, in which case the formed cushioning layer may afterward be bonded to the socket cup and/or the limb liner, using a suitable bonding agent such as an adhesive. In such cases, a release agent may be utilized to prevent bonding during the expanding and/or hardening process.

The ratio of the compounds mixed to form the filler material may determine the density (and the resilience) of the hardened (or cured) product. In many embodiments, the filler material consists of a single mixture having a compound ratio adapted to form, when hardened, a solid foam having a predetermined and substantially uniform density. In some embodiments, multiple mixtures, for example, mixtures having the same compounds but in different ratios, may be used, such as to selectively create regions of comparatively higher and lower density (which may, in turn, result in such regions having different degrees of resilience) in the cushioning layer.

Optionally, multiple mixtures of different compounds may be used. Methods employing multiple mixtures may find utility in applications such as those in which one or more pressure relief regions are formed in the cushioning layer, such as to accommodate sensitive areas of residual limb 10 (such as the skin surrounding a scar, areas of nerve damage, and so forth), and/or to create one or more support regions, such as to provide areas of greater rigidity in the cushioning layer, and so forth, as desired by the practitioner. In such methods, a first mixture may be applied to desired regions inside the socket cup, followed by application of a second mixture (or additional mixtures), with each subsequent mixture being added after the preceding mixture is allowed to partially or completely expand and/or harden, such as to create discrete and/or continuous regions of different densities in the cushioning layer. Thus, although cushioning layer 120 of example prosthetic socket device 100 is shown to be of a consistent and substantially uniform density throughout its entirety, other embodiments created in accordance with this disclosure may include a cushioning layer composed of multiple portions, or regions, of different densities.

In methods in which the filler material forms a bond between the liner and the socket cup, after the expanding and hardening process is complete, the socket cup, cushioning layer, and limb liner, as a unitary prosthetic socket device, may be removed from the residual limb, such as by rolling any portion of the limb liner that extends along the residual limb from the socket cup downward toward the distal end of the residual limb to break the friction lock between the internal surface of the limb liner and the skin of the residual limb. To assist removal, the user may optionally wear an additional covering over the residual limb, such as a thin-ply fabric liner, for the fitting process, such as to interfere with or weaken a friction lock between the limb liner and the residual limb.

Once the curing time is complete, the prosthetic socket device is ready for use. As such, the prosthetic socket device may be coupled to the prosthetic device with which the socket is to be used, either directly or indirectly, by suitable coupling means, which may be mounted, for example, on an exterior surface of the socket cup, such as shown in FIG. 1. As noted above, coupling means may be applied to the socket cup prior to or after the fitting process, according to the application, and may include one or means including mechanical, magnetic, and/or adhesive bonds, as appropriate.

The aforementioned process is illustrative in nature and includes several variations to the individual steps thereof, all of which are encompassed by the scope of this disclosure. Of course, additional variations are also possible without departing from this scope.

For example, the order of some of the steps may differ from as presented above, such as introducing the filler material into the socket cup prior to positioning the covered distal end region of the residual limb in place relative to the socket cup. Such a variation may be suitable in cases in which the exact position of the residual limb relative to the socket cup is not particularly crucial, such as to further minimize the time during which the residual limb must be braced in a particular position during the fitting process. In such a variation, as well as in processes in which filler material is introduced into the socket cup once the residual limb is positioned therein, additional steps may include adding additional filler material to the socket cup, such as to fill any remaining space between the limb liner and the socket cup, and/or removing any excess material, such as by trimming away filler material that has expanded beyond the top edge or lip of the socket cup.

In other variations, additional structural components may be used. For example, a reinforcing plate or similar structure may be placed against the floor (or another portion) of the socket cup prior to introducing the filler material, such as to provide additional structural strength to a mechanical coupling between the socket device and a prosthetic device coupled thereto.

The aforementioned processes may be employed to produce a prosthetic socket device more inexpensively and in substantially less time compared to traditional methods. Further, the aforementioned processes may largely be accomplished a single practitioner using readily available and comparatively inexpensive materials, in a manner that minimizes the fitting and processing time normally required to produce a prosthetic socket device according to traditional methods. As such, the aforementioned processes may have substantial benefit in areas in which the resources normally required by traditional methods are difficult to obtain or simply unavailable.

Although the present invention has been shown and described with reference to the foregoing operational principles and illustrated examples, embodiments, and methods, it will be apparent to those skilled in the art that various changes in form, detail, order, and otherwise, may be made without departing from the spirit and scope of the invention. The present invention is intended to embrace all such alternatives modifications and variances that fall within the scope of the appended claims.

We claim:

1. A method of producing a custom-fitted prosthetic socket device for a residual limb,
    the method comprising:
        covering at least the distal end region of the residual limb with a residual limb liner;
        positioning the covered distal end region of the residual limb at least partially within a socket cup, so that a spaced relationship between the exterior surface of the limb liner and the interior surface of the socket cup is maintained, the socket cup being fabricated from a rigid material and having a floor and a wall, a top edge of the wall forming an opening at a top end of the socket cup;
        introducing an expandable, hardenable filler material into the socket cup;
        expanding the filler material to fill the volume between the exterior surface of the limb liner and the interior surface of the socket cup;
        hardening the expanded filler material to a hardened condition; and
        removing the socket cup, the hardened filler material, and the limb liner, from the residual limb.

2. The method of claim 1, further including bonding the filler material with one or more of the interior surface of the socket cup and the exterior surface of the limb liner.

3. The method of claim 2, wherein bonding the filler material with one or more of the interior surface of the socket cup and the exterior surface of the limb liner occurs upon or after contact of the filler material with the respective surface during one or more of expanding and hardening the filler material.

4. The method of claim 3, wherein the exterior surface of the limb liner is porous, and wherein bonding the filler material with the exterior surface of the limb liner further includes at least partially permeating the exterior surface of the limb liner with the filler material.

5. The method of claim 2, wherein bonding the filler material with one or more of the interior surface of the socket cup and the exterior surface of the limb liner occurs after removing one or more of the socket cup, the hardened filler material, and the limb liner from the residual limb.

6. The method of claim 2, further including, prior to bonding, applying a bonding agent to one or more of the surfaces to be bonded.

7. The method of claim 1, wherein in a hardened condition the filler material forms a solid foam, and wherein the method further comprises producing the filler material from one or more mixtures each adapted to form, when hardened, a solid foam having a predetermined and substantially uniform internal density.

8. The method of claim 7, wherein introducing the filler material into the socket cup includes introducing two or more mixtures adapted to form, when the filler material hardens, a solid foam composed of at least two portions having different substantially uniform internal densities.

9. The method of claim 8, wherein portions having a comparatively greater internal density are less resilient than portions having a comparatively lower internal density.

10. The method of claim 8, wherein at least two of the two or more mixtures are mixtures that include two or more of the same compounds, but in different ratios.

11. The method of claim 8, wherein a first mixture is one or more of at least partially expanded, and at least partially hardened, prior to the introduction of a second mixture.

12. The method of claim 7, wherein the filler material includes an integral skinning polyurethane foam.

13. The method of claim 1, wherein positioning the covered distal end region of the residual limb within the socket cup precedes introducing the filler material.

14. The method of claim 1, wherein introducing the filler material precedes positioning the covered distal end region of the residual limb within the socket cup.

15. The method of claim 1, further comprising mounting coupling structure for a prosthetic device on an exterior surface of the socket cup.

16. The method of claim 1, wherein providing a socket cup includes selecting from a plurality of sized socket cups a socket cup appropriate to the physical configuration of the distal end region of the residual limb.

17. A method of producing a custom-fitted prosthetic socket device for a residual limb, the method comprising:
- selecting, from a plurality of open-ended socket cups, a socket cup appropriate to the physical configuration of the distal end region of the residual limb;
- covering the distal end region of the residual limb with a residual limb liner having a porous exterior surface;
- positioning the covered distal end region within the socket cup;
- introducing an expandable, hardenable tiller material into the socket cup;
- maintaining a spaced relationship between the exterior surface of the limb liner and the interior surface of the socket cup while allowing the tiller material to expand to fill the volume therebetween and at least partially permeate the porous exterior surface of the limb liner, and allowing the expanded filler material to harden to a resilient solid foam having a predetermined internal density, thereby forming a bond between the interior surface of the socket cup and the exterior surface of the limb liner;
- removing, as a unitary prosthetic socket device, the socket cup, the hardened filler material, and the partially embedded limb liner, from the residual limb; and
- coupling the prosthetic socket device to a prosthetic device.

18. The method of claim 17, wherein each of the plurality of open-ended socket cups is comprised of a substantially rigid material.

19. The method of claim 17, wherein the substantially rigid material is one or more of plastic and metal.

20. The method of claim 17, wherein each of the plurality of open-ended socket cups has a floor and a wall, a top edge of the wall defining a slight annular lip and forming an opening at a top end of the socket cup.

* * * * *